United States Patent
Gray et al.

(10) Patent No.: US 6,803,371 B2
(45) Date of Patent: Oct. 12, 2004

(54) PURINE INHIBITORS OF PROTEIN KINASES, G PROTEINS AND POLYMERASES

(75) Inventors: Nathanael S. Gray, Berkeley, CA (US); Peter Schultz, Oakland, CA (US); Sung-Hou Kim, Moraga, CA (US); Laurent Meijer, Roscoff (FR)

(73) Assignees: The Regents of the University of California, Oakland, CA (US); Centre National de la Recherche (FR)

( * ) Notice: Subject to any disclaimer, the term of this patent is extended or adjusted under 35 U.S.C. 154(b) by 0 days.

(21) Appl. No.: 10/352,752

(22) Filed: Jan. 27, 2003

(65) Prior Publication Data

US 2003/0176699 A1 Sep. 18, 2003

Related U.S. Application Data

(63) Continuation of application No. 09/847,007, filed on May 1, 2001, now Pat. No. 6,617,331, which is a continuation of application No. 09/130,255, filed on Aug. 6, 1998, now Pat. No. 6,255,485.

(60) Provisional application No. 60/055,400, filed on Aug. 7, 1997.

(51) Int. Cl.$^7$ ............... C07D 473/16; A61K 31/52; A61P 35/00
(52) U.S. Cl. ................. 514/263.4; 544/277
(58) Field of Search ................. 514/263.4; 544/277

(56) References Cited

U.S. PATENT DOCUMENTS

| | | | |
|---|---|---|---|
| 5,866,702 A | | 2/1999 | Mackman |
| 6,153,618 A | | 11/2000 | Schultz |
| 6,316,456 B1 | * | 11/2001 | Meijer et al. ............ 514/263.4 |
| 6,552,192 B1 | * | 4/2003 | Hanus et al. ................ 544/277 |
| 2003/0191312 A1 | * | 10/2003 | Ding et al. .................. 544/277 |
| 2004/0034224 A1 | * | 2/2004 | Hammarstrom et al. .... 544/277 |

FOREIGN PATENT DOCUMENTS

| | | |
|---|---|---|
| WO | WO 97/16452 A | 5/1997 |
| WO | WO 97/20842 A | 6/1997 |
| WO | WO 98/05335 A | 2/1998 |
| WO | WO 98/05335 * | 2/1998 |
| WO | WO 98/16528 A | 4/1998 |

OTHER PUBLICATIONS

De Azevedo, et al., Eur. J. Biochem., 243:518–526 (1997).
Gray, et al., Tetrahedron Letters, 38(7):1161–1164 (1997).
Havlicek, et al., J. Med. Chem., 40:408–412 (1997).
Schow, et al., Biorganic & Medicinal Chemistry Letters, 7(21):2697–2702 (1997).
Vessely, et al., Eur. J. Biochem., 224:771–786 (1994).
Norman, JACS, 118:7430 (1996).
Cheng, Chemistry & Biology, 6(6):361–375 (1999).

* cited by examiner

*Primary Examiner*—Mark L. Berch
(74) *Attorney, Agent, or Firm*—Townsend & Townsend & Crew LLP

(57) ABSTRACT

The present invention relates to 2-N-substituted 6-(4-methoxybenzylamino)-9-isopropylpurines that inhibit, inter alia, protein kinases, G-proteins and polymerases. In addition, the present invention relates to methods of using such 2-N-substituted 6-(4-methoxybenzylamino)-9-isopropylpurines to inhibit protein kinases, G-proteins, polymerases and other cellular processes and to treat cellular proliferative diseases.

4 Claims, 2 Drawing Sheets

PURINE INHIBITORS OF PROTEIN KINASES, G PROTEINS AND POLYMERASES

This application is a continuation of U.S. application Ser. No. 09/847,007, filed May 1, 2001, now U.S. Pat. No. 6,617,331, which is a continuation of application Ser. No. 09/130,255, flied Aug. 6, 1998, now U.S. Pat. No. 6,255,485 which is a non-provisional of and claims the benefit of U.S. Provisional Application No. 60/055,400, filed Aug. 7, 1997. Each of these applications is incorporated by reference in their entirety and for all purposes.

GOVERNMENT RIGHTS

This invention was made with Government support under Grant (Contract) No. DE-AC03-76SF00098 awarded by the U.S. Department of Energy. The Government has certain rights in this invention.

FIELD OF THE INVENTION

The present invention relates to purine analogs that inhibit, inter alia, protein kinases, G-proteins and polymerases. In addition, the present invention relates to methods of using such purine analogs to inhibit protein kinases, G-proteins, polymerases and other cellular processes and methods of using such purine analogs to treat, for example, cellular proliferative diseases and neurodegenerative diseases.

BACKGROUND OF THE INVENTION

Phosphorylation of serine, threonine and tyrosine residues by protein kinases represents one of the most common post-translational regulatory modifications of proteins. More than 200 protein kinases have been described, following either purification to homogeneity or molecular cloning (see, Hunter, T. (1991), *Methods Enzymol.*, 200:3–37; Hanks, S. K., et al. (1991), *Methods Enzymol.*, 200:38–81; Hanks, S. K. 1991), *Curr. Opin. Struct. Biol.*, 1:369–383; and Hubbard, M. J., et al. (1993) *Trends Biochem. Sci.*, 18:172–177). It is thought that as much as 2–3% of eukaryotic genes encode protein kinases. The importance of protein kinases in physiological processes has stimulated an active search for specific inhibitors with potential pharmacological interest (see, Hidaka, H., et al. (1992), *Annu. Rev. Pharmacol. Toxicol.*, 32:377–397). Several classes of compounds have been identified, such as staurosporine, naphthalene sulfonamides (W7, ML-9, SC-9), isoquinoline derivatives (H-7, H-8, KN-62), sphingosine, tyrphostins and others, but in most cases these inhibitors display broad specificity. Only some pseudosubstrate autoinhibitory peptides show a high degree of specificity.

Cyclin-dependent kinases (CDK), in particular, have recently raised considerable interest in view of their essential role in the regulation of the cell division cycle (CDC) (see, Nigg, E. A. (1993), *Trends in Cell Biol.*, 3:296–301; and Sherr, C. S. (1993), *Cell*, 73:1059–1065). CDKs are highly conserved among eukaryotic species. Higher eukaryotic cells contain several isoforms of CDKs that become activated in specific phases of the cell cycle. CDKs consist of a catalytic subunit, the prototype of which is CDC2, and a regulatory subunit (cyclin). Six human CDK proteins have been described so far (see, Meyerson, M., et al. (1992), *EMBO J.*, 11:2909–2917; Meyerson, M., et al. (1994), *Mol. Cell. Biol.*, 14:2077–2086; and Van den Heuvel, S., et al. (1993), *Science*, 262:2050–2054), namely, CDK1 (also known as CDC2) and CDK2-6. With the exception of CDK3, for which the regulatory cyclin has not yet been identified, all these CDKs proteins are regulated by the transient association with one member of the cyclin family, i.e., cyclin A (CDC2, CDK2), B1–B3 (CDC2), D1–D3 (CDK2, CDK4, CDK5, CDK6), E (CDK2). Each step of the cell cycle is thought to be regulated by such CDK complexes: G1/S transition (CDK2/cyclin E, CDK3/unknown cyclin, CDK4/cyclin D1–D3, CDK6/cyclin D3), S phase (CDK2/cyclin A), G2 (CDC2/cyclin A), G2/M transition (CDC2/cyclins B).

CDKs are able to phosphorylate many proteins that are involved in cell cycle events, including histones, lamins and tumor suppressor proteins, such as the retinoblastoma gene product pRb (see, Norbury, C., et al., supra, Matsushime, H., et al. (1992), *Cell*, 71:323–334, Nigg, E. E. (1993), *Curr. Opin. Cell. Biol.*, 5:187–193). In accordance with their central role in the cell cycle, enzyme activity is tightly controlled by multiple mechanisms. Kinase activation requires complex formation with regulatory cyclin proteins as described above, followed by an activating phosphorylation on Thr-161 in CDC2 or the corresponding Thr in the other CDKs (see, e.g., Gould, K. L., et al. (1991), *EMBO J.*, 10:3297–3309; Desai, D., et al. (1992), *Mol. Biol. Cell*, 3:571–582; Solomon, M. J., et al. (1992), *Mol. Biol. Cell*, 3:13–27). In addition, enzyme activity is negatively regulated by phosphorylations at Tyr-15 and/or Thr-14 (see, e.g., Solomon, M. J., et al., supra; Gu, Y., et al. (1992), *EMBO J.*, 11:3995–4005; Krek, W., et al. (1991), *EMBO J.*, 10:3331–3341; Norbury, C., et al. (1991), *EMBO J.*, 10:3321–3329; Parker, L. L., et al. (1992), *Proc. Natl. Acad. Sci. U.S.A.*, 89:2917–2921; McGowan, C. H., et al. (1993), *EMBO J.*, 12:75–85), or by complex formation with inhibitor proteins like p16 (see, Serrano, M., et al. (1993), *Nature* (London), 366:704–707; Kamb, A., et al. (1994), *Nature* (London), 264:436–440; Nobori, T., et al. (1994), *Nature* (London), 368:753–756), p27 (see, Polyak, K., et al. (1994), *Cell*, 78:59–66; Toyoshima, H., et al. (1994), *Cell*, 78:67–74), p28 (see, Hengst, L., et al. (1994), *Proc. Natl. Acad. Sci. U.S.A.*, 91:5291–5295) and p21 (see, Gu, Y., et al. (1993), *Nature* (London), 366:707–710; Xiiong, Y., et al. (1993), *Nature* (London), 366:701–704; Harper, J. W., et al. (1993), *Cell*, 75:805–816; Dulic, V., et al. (1994), *Cell*, 76:1013–1023), the latter being inducible by p53. Especially noteworthy is the fact that deletions of the p16 gene were found in over 50% of all human malignant cell lines tested (see, Kamb, A., supra, Nobori, T., et al., supra), although much less in primary tumor cells (see, Spruck III, C. H., et al. (1994), *Nature* (London), 370:183–184), implicating p16 functions as tumor suppressor protein. Thus, both the cell growth signals transmitted through many oncogene products and the growth inhibitory signals from several tumor suppressor proteins modulate the activity of CDKs. Although mutations in CDKs themselves have not been associated with cancer, cyclin overexpression has been linked to tumorigenesis (see, Hunter, T., et al. (1991), *Cell*, 66:1071–1074; Keyomarsi, K., et al. (1993), *Proc. Natl. Acad. Sci. U.S.A.*, 90:1112–1116; Wang, T. C., et al. (1994), *Nature* (London), 369:669–671.) Hence, CDKs are a promising target for developing inhibitors with antineoplastic effects and for the treatment of cell-proliferative diseases.

The purine ring system is a key structural element of the substrates and ligands of many biosynthetic, regulatory and signal transduction proteins including cellular kinases, G proteins and polymerases. As such, the purine ring system has been a good starting point in the search for inhibitors of many biomedically significant processes. In fact, while purine analogs were being screened for inhibition of various protein kinases, a relatively selective inhibitor, olomoucine (FIG. 1), was identified that competitively inhibits CDK2/cyclin A with an IC$_{50}$ of 7 iM (see, Vesely, J., et al., (1994) *Eur. J. Biochem.*, 224:771–786). Although olomoucine exhibits moderate inhibitory activity and good selectivity for the CDK/cyclin protein kinases, it would be advantageous to identify other purine analogs that have increased affinity and specificity for protein kinases as well as G proteins and polymerases. Quite surprisingly, the present invention provides such analogs.

SUMMARY OF THE INVENTION

The present invention provides (i) purine analogs that, inter alia, inhibit protein kinases, G proteins and polymerases; (ii) methods of using such purine analogs to inhibit protein kinases, G proteins, polymerases and other cellular processes; and (iii) pharmaceutical compositions comprising such purine analogs.

In one embodiment, the present invention provides purine analogs having the generally formula:

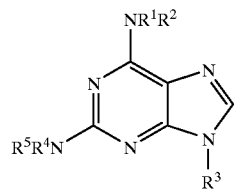

I or a pharmaceutically acceptable salt thereof.

In Formula I, $R^1$, $R^2$, $R^4$ and $R^5$ are independently selected and are functional groups including, but not limited to, H, $C_1$–$C_8$ straight-chain, branched-chain, saturated and unsaturated alkyl, $C_1$–$C_8$ straight-chain, branched-chain, saturated and unsaturated substituted alkyl, aryl and substituted aryl.

In another embodiment, the present invention provides pharmaceutical compositions comprising the purine analog compounds of the invention and a pharmaceutically acceptable carrier.

In another embodiment, the present invention provides a method of inhibiting a protein selected from the group consisting of protein kinases, G proteins and polymerases, the method comprising contacting the protein with a purine analog of the present invention. In a preferred embodiment, the protein is a protein kinase. In an even more preferred embodiment, the protein kinase is a cyclin-dependent kinase. In an even more preferred embodiment, the cyclin-dependent kinase is a member selected from the group consisting of CDK1 (CDC2), CDK2, CDK3, CDK4, CDK5, CDK6, CDK7 and CDK8 and, in particular, CDK1 and CDK5.

In another embodiment, the present invention provides a method of treating a cellular proliferative disease, the method comprising administering to a mammal having the disease a therapeutically effective amount of a purine analog of the present invention.

In yet another embodiment, the present invention provides a method of inhibiting the growth of a tumor cell, the method comprising contacting the tumor cell with a purine analog of the present invention. In a preferred embodiment, the tumor cell is selected from the group consisting of lung, colon, breast, ovarian, prostate and hepatic cells. In a preferred embodiment, the tumor cell is in a mammalian subject. In another preferred embodiment, the purine analog is formulated in a pharmaceutically acceptable form with an excipient or carrier and administered orally. In another embodiment, this method further comprising the step of observing for a reduction in the growth of a tumor cell.

In still another embodiment, the present invention provides a method of treating a neurodegenerative disease, the method comprising administering to a mammal having the disease a therapeutically effective amount of a purine analog of the present invention.

Other features, objects and advantages of the invention and its preferred embodiments will become apparent from the detailed description which follows.

DETAILED DESCRIPTION OF THE INVENTION AND PREFERRED EMBODIMENTS

Figure 1:
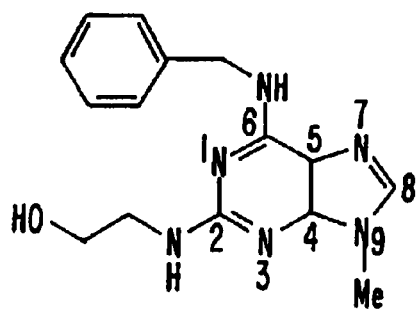
FIG. 1 sets forth the structure of olomoucine and the numbering scheme for the purine nucleus.

The present invention provides (i) purine analogs that, inter alia, inhibit protein kinases, G proteins and polymerases; (ii) methods of using such purine analogs to inhibit protein kinases, G proteins, polymerases and other cellular processes; and (iii) pharmaceutical compositions comprising such purine analogs.

A. Definitions

The term "independently selected" is used herein to indicate that the R groups, e.g., $R^1$, $R^2$, $R^4$ and $R^5$, can be identical or different (e.g., $R^1$, $R^2$ and $R^3$ may all be substituted alkyls or $R^1$ and $R^2$ may be a substituted alkyl and $R^3$ may be an aryl, etc.).

A named R group will generally have the structure which is recognized in the art as corresponding to R groups having that name. For the purposes of illustration, representative R groups as enumerated above are defined herein. These definitions are intended to supplement and illustrate, not preclude, the definitions known to those of skill in the art.

The term "alkyl" is used herein to refer to a branched or unbranched, saturated or unsaturated, monovalent hydrocarbon radical having from 1–12 carbons and preferably, from 1–6 carbons. When the alkyl group has from 1–6 carbon atoms, it is referred to as a "lower alkyl." Suitable alkyl radicals include, for example, methyl, ethyl, n-propyl, i-propyl, 2-propenyl (or allyl), n-butyl, t-butyl, i-butyl (or 2-methylpropyl), etc.

"Substituted alkyl" refers to alkyl as just described including one or more functional groups such as lower alkyl, aryl, acyl, halogen (i.e., alkylhalos, e.g., $CF_3$), hydroxy, amino, alkoxy, alkylamino, acylamino, acyloxy, aryloxy, aryloxyalkyl, mercapto, both saturated and unsaturated cyclic hydrocarbons, heterocycles and the like. These groups may be attached to any carbon of the alkyl moiety.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, naphthyl, biphenyl, diphenylmethyl and benzophenone among others.

The term "arylalkyl" is used herein to refer to a subset of "aryl" in which the aryl group is attached through an alkyl group as defined herein.

"Substituted aryl" refers to aryl as just described including one or more functional groups such as lower alkyl, acyl, halogen, alkylhalos (e.g., CF₃), hydroxy, amino, alkoxy, alkylamino, acylamino, acyloxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. The term "substituted aryl" encompasses "substituted arylalkyl."

"Substituted arylalkyl" defines a subset of "substituted aryl" wherein the substituted aryl group is attached to the nucleus by an alkyl group as defined herein.

The term "halogen" is used herein to refer to fluorine, bromine, chlorine and iodine atoms.

The term "hydroxy" is used herein to refer to the group —OH.

The term "amino" is used herein to refer to the group —NRR', where R and R' may independently be hydrogen, lower alkyl, substituted lower alkyl, aryl, substituted aryl or acyl.

The term "alkoxy" is used herein to refer to the —OR group, where R is a lower alkyl, substituted lower alkyl, aryl, substituted aryl, arylalkyl or substituted arylalkyl wherein the alkyl, aryl, substituted aryl, arylalkyl and substituted arylalkyl groups are as described herein. Suitable alkoxy radicals include, for example, methoxy, ethoxy, phenoxy, substituted phenoxy, benzyloxy, phenethyloxy, t-butoxy, etc.

The term "alkylamino" denotes secondary and tertiary amines wherein the alkyl groups may be either the same or different and may consist of straight or branched, saturated or unsaturated hydrocarbons.

The term "heterocyclic" is used herein to describe a monovalent group having a single ring or multiple condensed rings from 1–12 carbon atoms and from 1–4 heteroatoms selected from nitrogen, sulfur or oxygen within the ring. Such heterocycles are, for example, tetrahydrofuran, morpholine, piperidine, pyrrolidine, thiophene, pyridine, isoxazole, phthalimide, pyrazole, indole, furan, benzo-fused analogs of these rings, etc.

The term "substituted heterocyclic" as used herein describes a subset of "heterocyclic" wherein the heterocycle nucleus is substituted with one or more functional groups such as lower alkyl, acyl, halogen, alkylhalos (e.g., CF₃), hydroxy, amino, alkoxy, alkylamino, acylamino, acyloxy, mercapto, etc.

The term "pharmaceutically acceptable salt" refers to those salts of compounds which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, ptoluenesulfonic acid, salicylic acid and the like. Pharmaceutically acceptable salts include, for example, alkali metal salts, such as sodium and potassium, alkaline earth salts and ammonium salts.

The term "contacting" is used herein interchangeably with the following: combined with, added to, mixed with, passed over, incubated with, flowed over, etc. Moreover, the purine compounds of present invention can be "administered" by any conventional method such as, for example, parenteral, oral, topical and inhalation routes as described herein.

"An amount sufficient" or "an effective amount" is that amount of a given purine analog which exhibits the binding/inhibitory activity of interest or, which provides either a subjective relief of a symptom(s) or an objectively identifiable improvement as noted by the clinician or other qualified observer.

B. Purine Analogs

The purine ring is a key structural element of the substrates and ligands of many biosynthetic, regulatory and signal transduction proteins including cellular protein kinases, G proteins and polymerases. Quite importantly, the present invention provides purine analogs which can be used to inhibit such proteins and, thus, many biomedically important processes. More particularly, the present invention provides purine analogs that inhibit, inter alia, protein kinases, G proteins, polymerases and other cellular processes. As such, the purine analogs of the present invention can be used to block cell-cycle progression, cellular proliferation, apoptosis as well as other cellular processes. The purine analogs of the present invention are active in the subnanomolar and submicromolar ranges.

In one embodiment, the present invention provides purine analogs having the generally formula:

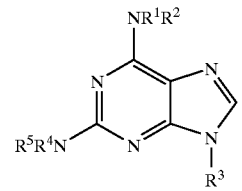

I or a pharmaceutically acceptable salt thereof.

In Formula I, $R^1$, $R^2$, $R^4$ and $R^5$ are independently selected and are functional groups including, but not limited to, H, $C_1$–$C_8$ straight-chain, branched-chain, saturated and unsaturated alkyl, $C_1$–$C_8$ straight-chain, branched-chain, saturated and unsaturated substituted alkyl, aryl and substituted aryl.

Within the scope of the above Formula I, certain embodiments are preferred, namely those in which $R^1$ and $R^2$ are independently selected and are functional groups including, but not limited to, H, aryl, substituted aryl, $C_1$–$C_8$ straight-chain, saturated alkyl substituted with aryl and $C_1$–$C_8$ straight-chain, saturated alkyl substituted with substituted aryl; $R^3$ is a functional group including, but not limited to, $C_1$–$C_8$ branched-chain saturated alkyl and $C_1$–$C_8$ branched-chain unsaturated alkyl; and $R^4$ and $R^5$ are independently selected and are functional groups including, but not limited to, H, $C_1$–$C_8$ straight-chain, branched-chain, saturated and unsaturated alkyl, $C_1$–$C_8$ straight-chain, branched-chain, saturated and unsaturated substituted alkyl, aryl and substituted aryl.

In another preferred embodiment, $R^1$ and $R^2$ are independently selected and are functional groups including, but not limited to, H, unsubstituted aryl and substituted aryl; $R^3$ is isopropyl; and $R^4$ and $R^5$ are independently selected and are functional groups including, but not limited to, H, $C_1$–$C_8$ saturated and unsaturated branched-chain alkyl and $C_1$–$C_8$ saturated and unsaturated branched-chain substituted alkyl.

In another preferred embodiment, $R^4$ and $R^5$ are independently selected and are functional groups including, but not limited to, H, and

wherein X is a member selected from the group consisting of H, OH, CH₂OH, C(O)NH₂, SH, COOH or a pharmaceutically acceptable salt thereof and COOR⁷, wherein R⁷ is lower alkyl; and $R^6$ is a member selected from the group consisting of H, $C_1$–$C_8$ straight-chain alkyl, $C_1$–$C_8$ branched-chain alkyl, $C_1$–$C_8$ straight-chain substituted alkyl, $C_1$–$C_8$ branched-chain substituted alkyl.

With respect to above embodiment, X is preferably COOH; and $R^6$ is independently selected and is a functional group including, but not limited to, H, —$CH_3$, —$(CH_2)_3$NHC(=NH)$NH_2$, —$CH_2CONH_2$, —$CH_2CO_2H$, —$CH_2SH$, —$(CH_2)_2CONH_2$, —$(CH_2)_2CO_2H$, —$CH_2$(4-imidazoyl), —$CH(CH_3)CH_2CH_2$, —$CH_2CH(CH_3)_2$, —$(CH_2)_4NH_2$, —$(CH_2)_2SCH_3$, —$CH_2Ph$, —$CH_2OH$, —$CH(CH_3)OH$, —$CH_2$(3-indolyl), —$CH_2$(4-hydroxyphenyl) and —$CH(CH_3)_2$.

In such embodiments, $R^1$ and $R^2$ are independently selected and are functional groups including, but not limited to, H and aryl substituted in at least one of positions 3, 4, 5 with a member independently selected from the group consisting of halogen, alkoxy, trihalomethyl, amino, hydroxyl, thiol, sulfonic acid, sulfonic acid, amide, ester and carboxylic acid.

Table 1 sets forth purine compounds in accordance with the present invention which are particularly preferred. The compounds in this table and throughout this specification are referred to by code numbers, which are used for convenience only, and are strictly arbitrary for purposes of this invention.

TABLE 1

Exemplary Purine Analogs

| Structure | Code Name | $IC_{50}$ cdc2/cyclinB (additional kinases) |
|---|---|---|
| Class 1 | | |
| 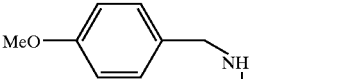 | NG-30 | 330 nM<br>2000 nM(CDK2/cyclinE)<br>>33,000 nM(GSK-3)<br>8,000 nM(erk1) |
| Class 2a | | |
| 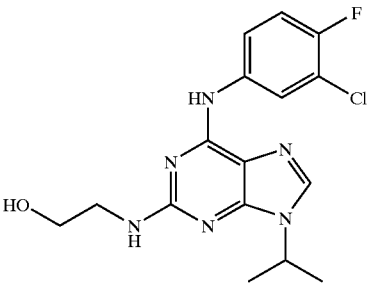 | NG-64 | 290 nM |
| 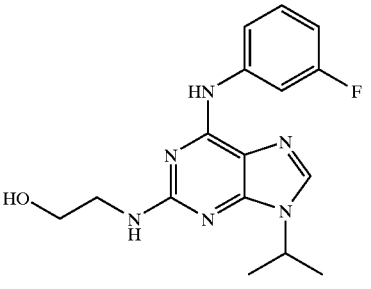 | NG-65 | 400 nM |

TABLE 1-continued

Exemplary Purine Analogs

| Structure | Code Name | IC$_{50}$ cdc2/cyclinB (additional kinases) |
|---|---|---|
| (2-hydroxyethylamino at C2, phenylamino at C6, 9-isopropyl purine) | NG-42 | 4300 nM |
| (2-hydroxyethylamino at C2, 2-chlorophenylamino at C6, 9-isopropyl purine) | NG-43 | 4300 n5M |
| (2-hydroxyethylamino at C2, 3-methoxyphenylamino at C6, 9-isopropyl purine) | NG-44 | 500 nM |
| (2-hydroxyethylamino at C2, 3-bromophenylamino at C6, 9-isopropyl purine) | NG-45 | 270 nM |
| (2-hydroxyethylamino at C2, 2-methoxyphenylamino at C6, 9-isopropyl purine) | NG-46 | 9000 nM |

TABLE 1-continued
Exemplary Purine Analogs
| Structure | Code Name | IC$_{50}$ cdc2/cyclinB (additional kinases) |
|---|---|---|
| 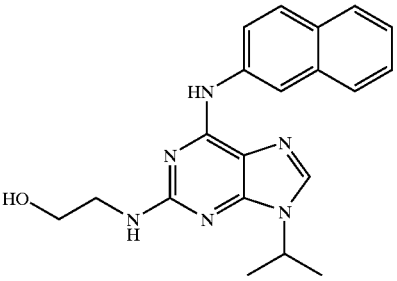 | NG-47 | 430 nM |
| 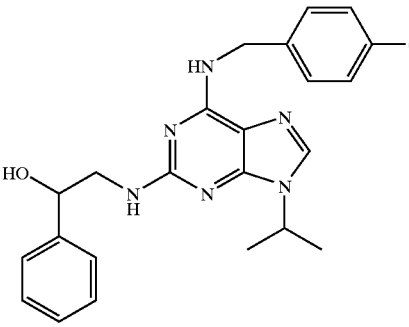 | NG-50 | 2800 nM |
| 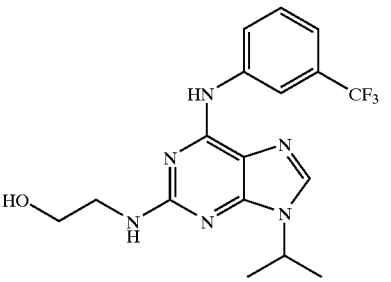 | NG-51 | 420 nM |
| 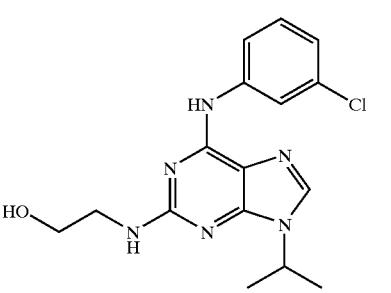 | NG-52 | 220 nM |
| 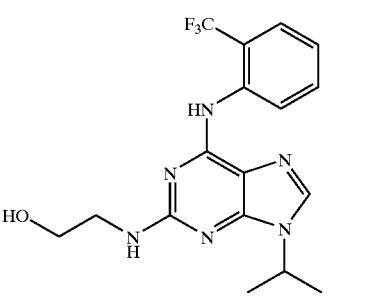 | NG-53 | 10,000 nM |

TABLE 1-continued

Exemplary Purine Analogs

| Structure | Code Name | IC$_{50}$ cdc2/cyclinB (additional kinases) |
|---|---|---|
| [structure: 6-(2,4-dichlorophenylamino)-2-(2-hydroxyethylamino)-9-isopropylpurine] | NG-54 | 2700 nM |

Class 2b

| Structure | Code Name | IC$_{50}$ cdc2/cyclinB (additional kinases) |
|---|---|---|
| [structure: 6-(4-methoxybenzylamino)-2-(1-hydroxymethyl-2-methylpropylamino, ±)-9-isopropylpurine] | NG-35 | 150 nM<br>140(cdk2/cyclinE)<br>15 nM(cdk5/p25)<br>4500(GSK-3)<br>3000(erk1) |
| [structure: 6-(4-methoxybenzylamino)-2-(1-hydroxymethyl-2-methylpropylamino, S)-9-isopropylpurine] | NG-76 | 600 nM<br>400(CDK2/cyclinE) |
| [structure: 6-(4-methoxybenzylamino)-2-(1-hydroxymethyl-2-methylpropylamino, R)-9-isopropylpurine] | NG-75 | 230 nM<br>140(CDK2/cyclinE) |
| [structure: 6-(4-methoxybenzylamino)-2-(1-hydroxymethylpropylamino, R)-9-isopropylpurine] | NG-33 | 130 nM<br>80 nM(CDK2/cyclinE)<br>20,000 nM(GSK-3)<br>>10,000 nM(erk1) |

TABLE 1-continued

Exemplary Purine Analogs

| Structure | Code Name | IC$_{50}$ cdc2/cyclinB (additional kinases) |
|---|---|---|
| | NG-36 | 100 nM<br>100 nM(cd2/cyclinE)<br>13,000 nM(GSK-3)<br>>10,000 nM(erk1) |

Class 2c

| Structure | Code Name | IC$_{50}$ cdc2/cyclinB (additional kinases) |
|---|---|---|
| 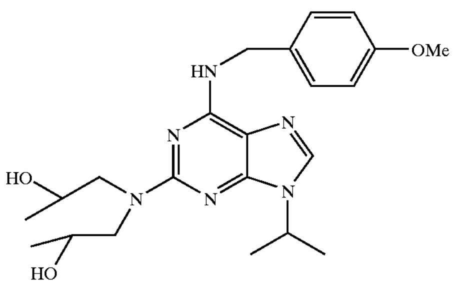 | NG-16 | 240 nM<br>180 nM(CDK2/cyclinE)<br>23,000 nM(GSK-3)<br>50,000 nM(erk1) |
| 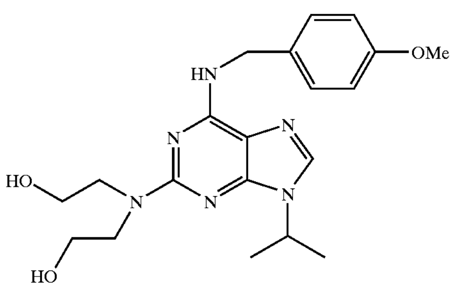 | NG-26 | 330 nM<br>230 nM(CDK2/cyclinE)<br>>33,000 nM(GSK-3)<br>33,000 nM(erk1) |
| 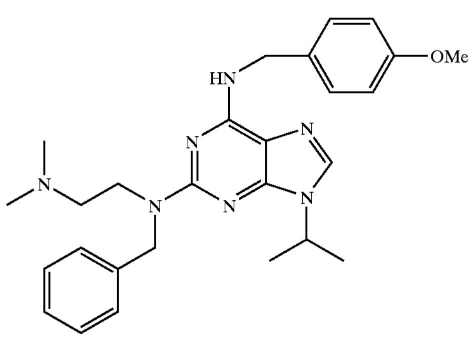 | NG-40 | 600 nM |

TABLE 1-continued

Exemplary Purine Analogs

| Structure | Code Name | IC$_{50}$ cdc2/cyclinB (additional kinases) |
|---|---|---|
| | NG-49 | 2800 nM |

Class 3

| Structure | Code Name | IC$_{50}$ cdc2/cyclinB (additional kinases) |
|---|---|---|
| 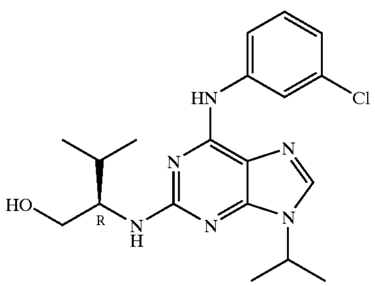 | NG-60 | 35 nM<br>30 nM(CDK2/CyclinE) |
| 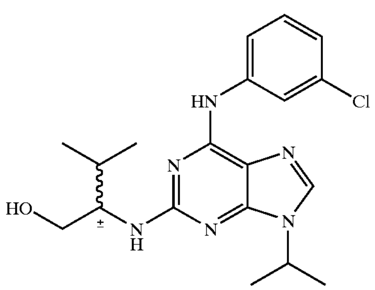 | NG-56 | 35 nM<br>55 nM(CDK2/CyclinE) |
| 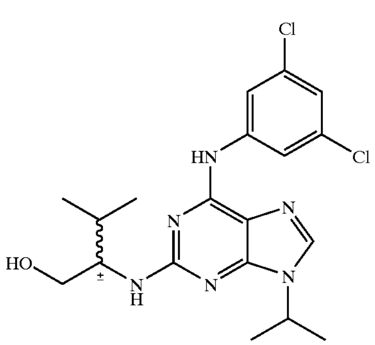 | NG-57 | 400 nM |

TABLE 1-continued

Exemplary Purine Analogs

| Structure | Code Name | IC$_{50}$ cdc2/cyclinB (additional kinases) |
|---|---|---|
| 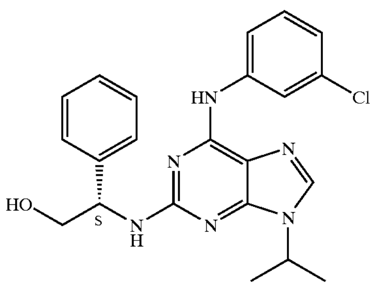 | NG-59 | 800 nM |
| 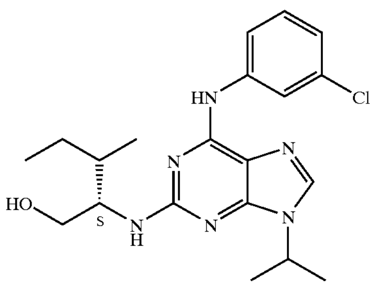 | NG-62 | 500 nM |
| 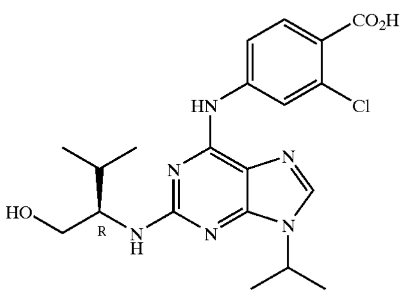 | NG-95 | approx. 20 nM |
| 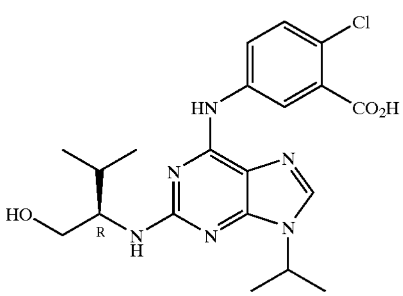 | NG-96 | approx. 30 nM |
| 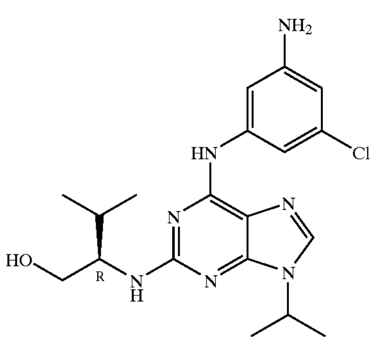 | NG-97 | 30 nM |

TABLE 1-continued

Exemplary Purine Analogs

| Structure | Code Name | IC$_{50}$ cdc2/cyclinB (additional kinases) |
|---|---|---|
| 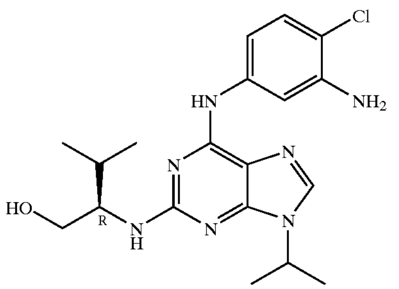 | NG-98 | 30 nM |
| 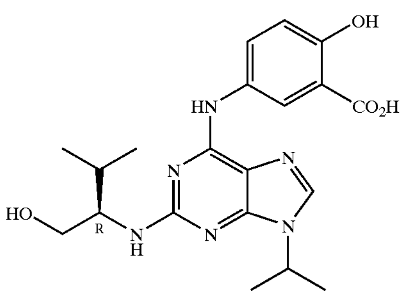 | NG-94 | approx. 100 nM |
| 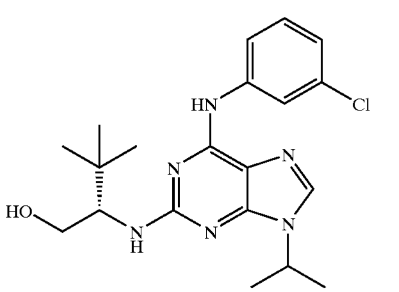 | NG-61 | 2300 nM |

Figure 2:
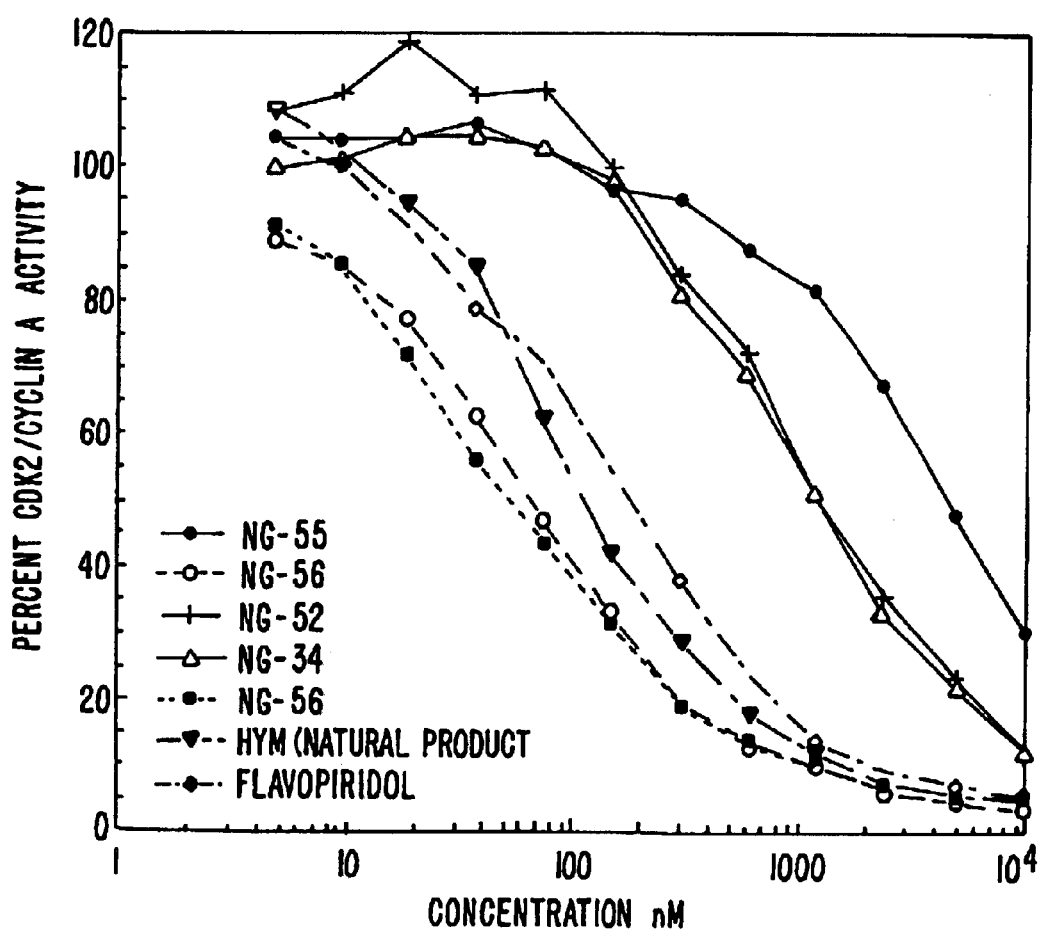
FIGS. 2 and 3 illustrate the IC$_{50}$ for representative compounds from Table 1.
Figure 3:
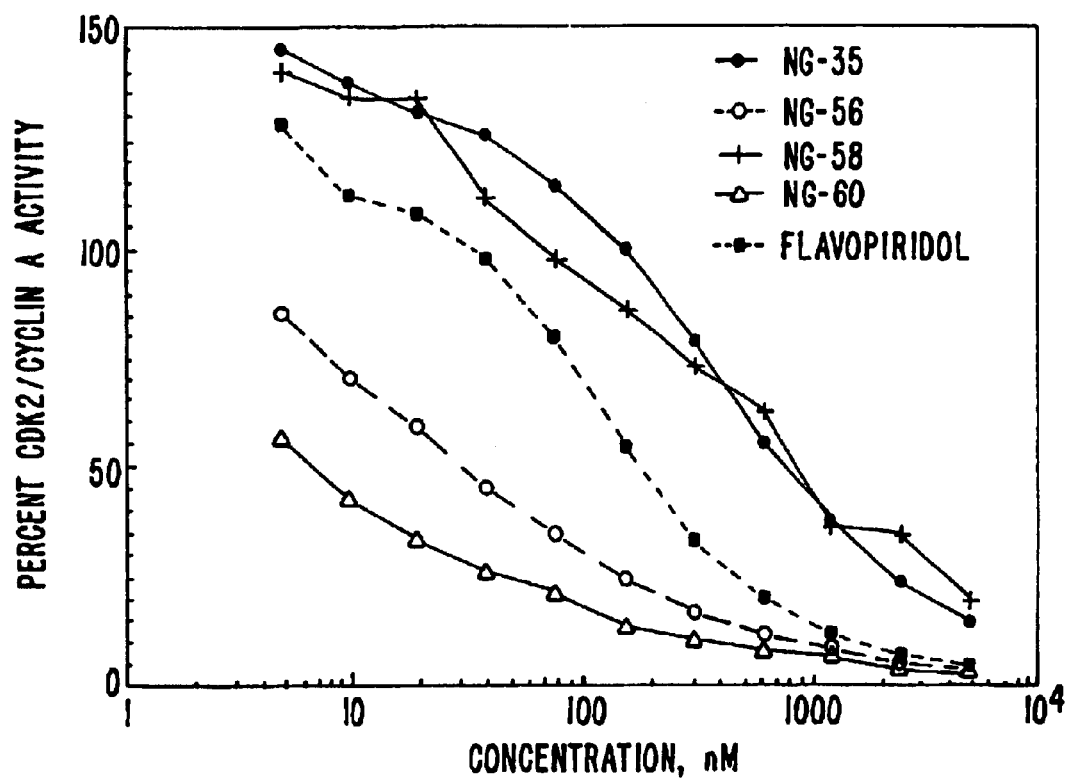

[a]These IC$_{50}$s can be compared with other known small molecule inhibitors of CDK2 (see, FIGS. 2 and 3).

It will be readily appreciated by those of skill in the art that depending on the substituents, the purine analogs of the present invention can be a racemic mixture or either of a pair of diastereomers or enantiomers.

The purine analogs of the present invention can be synthesized in a variety of ways, using conventional synthetic chemistry techniques. Typically, the compounds of the present invention are prepared according to the reaction scheme set forth in Scheme I, wherein $R^1$, $R^2$, $R^3$, $R^4$, and $R^5$ are as defined above. The use of appropriate organic solvents, temperature and time conditions for running the reactions are within the level of skill in the art. Reactions of this type are generally described by Norman, et al., *J. Am. Chem. Soc.* 118:7430–7431 (1996); and Gray, et al., *Tetrahedron Letters*, 38:1161–1164 (1997), the teachings of which are incorporated herein by reference. Moreover, suitable synthesis reactions are illustrated herein by the representative examples. Necessary starting materials can be obtained by standard procedures of organic chemistry.

SCHEME 1

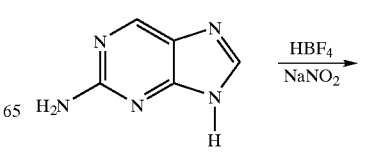

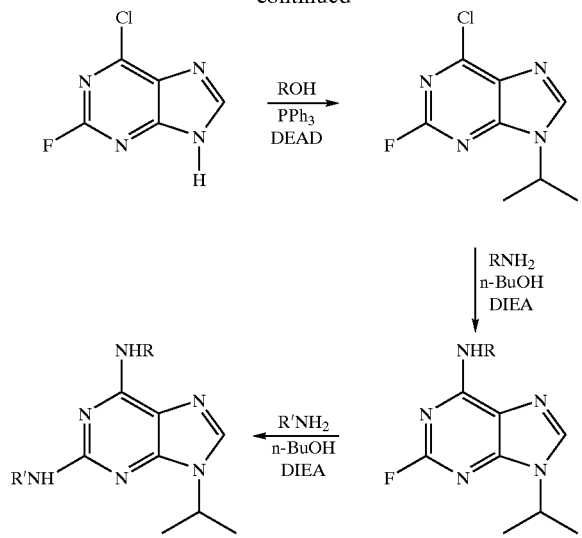

Briefly, as illustrated in Scheme I, a purine derivative with a halogen at the 2-position is alkylated at the 9-position with an alcohol using the Mitsonubo alkylation. Following the alkylation, the purine derivative is aminated at the 6-position with an amine. Once prepared, the purine analogs can be purified (e.g., by TLC), characterized (e.g., by Reverse Phase HPLC) and analyzed (e.g., by high resolution spectroscopy using, for example, $^1$H NMR or FAB-MS).

C. Uses for the Purine Analogs of the Present Invention

The purine analogs of the present invention can be used either in vitro or in vivo for a variety of purposes. As mentioned, the purine analogs of the present invention can be used to inhibit protein kinases, G proteins and polymerases. Moreover, the purine analogs of the present invention can be used to treat cellular-proliferative diseases. In addition, the compounds of the present invention can be used as molecular tools and molecular probes.

As such, in one embodiment, the present invention provides a method of inhibiting a protein kinase, a G protein or a polymerase, the method comprising contacting the protein kinase, the G protein or the polymerase with a purine analog having the general formula:

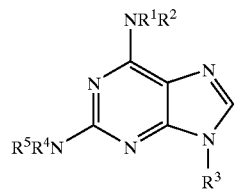

I or a pharmaceutically salt thereof. The prior discussions pertaining to $R^1$, $R^2$, $R^4$, $R^5$ and $R^6$, their definitions and preferred embodiments are fully applicable to the purine analogs used in this method and, thus, will not be repeated. The protein kinase, G protein or polymerase is contacted with the purine analog in an amount sufficient to effect inhibition.

Protein kinases which can be inhibited using the purine analogs of the present invention include, but are not limited to, cyclin-dependent kinases (CDKs), MAP kinases (p38, ERK), (MAPK/MEK/MEKK), cAMP-dependent kinase, c-GMP-dependent kinase, Calmodulin-dependent kinase, CSK (C-src like kinase) pp 60 c-src, myosin light chain kinase, JNK kinase, IKB kinase, Protein kinase C, etc. In a presently preferred embodiment, the protein kinase is a CDK. Such CDKs include CDK1 (or, interchangeably, CDC2) and CDK2–CDK8. In an even more preferred embodiment, the CDK is CDC2, CDK2 or CDK5 as many of the purine analogs of the present invention exhibit increased affinity and specificity with respect to these CDKs. G proteins can be inhibited using the compounds of the present invention include, but are not limited to, GTP binding proteins. Polymerases which can be inhibited using the purine analogs of the present invention include, but are not limited to, DNA polymerase á, DNA polymerase ó, DNA topoisomerase I, topoisomerase II, phosphatases, telomerases, etc. Other protein kinases, G proteins and polymerases which can be inhibited using the purine analogs of the present invention will be known to those of skill in the art.

Purine analogs of the present invention suitable for use in inhibiting protein kinases, G proteins or polymerase can readily be identified using in vitro and in vivo screening assays. For instance, purine analogs having protein kinase inhibitory activity can be screened for using the CDK2/CYCLIN A microtiter-based solution-phase protein kinase assay described in the examples and by Buxbaum, J. D., et al. *Anal. Biochem.* 1988, 169:209–215. Similarly, numerous assays exist which can be used to screen a given purine analog for G protein inhibitory activity or polymerase inhibitory activity. Such assays are described, for example, by Vesley, J., et al., *Eur. J. Biochem.*, 1994, 224:771–786, the teachings of which are incorporated herein by reference. Other assays known to and used by those of skill in the art can also be used to screen a given purine analog for inhibitory properties against protein kinases, G proteins and polymerases.

In addition, the purine analogs of the present invention can be used to treat cellular-proliferative disease, the method comprising administering to a mammalian subject having a cellular-proliferative disease a therapeutically effective amount of a purine analog having the general formula:

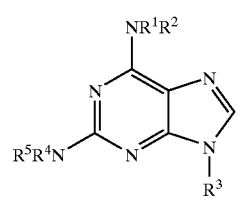

I or a pharmaceutically salt thereof. The prior discussions pertaining to $R^1$, $R^2$, $R^4$, $R^5$ and $R^6$, their definitions and preferred embodiments are fully applicable to the purine analogs used in this method and, thus, will not be repeated.

Cellular proliferative diseases which can be treated using the purine analogs of the present invention include, but are not limited to, abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying, for example, rheumatoid arthritis, psoriasis, diabetic retinopathy, other ocular angiogenic diseases such as retinopathy of prematurity (retrolental fibroplastic), macular degeneration, corneal graft rejection, neuroscular glaucoma and Oster Webber syndrome, psoriasis, restinosis, fungal, parasitic and viral infections such cytomegaloviral infections.

In a preferred embodiment, the present invention provides a method of inhibiting the growth of a tumor cell, the method comprising contacting the tumor cell with a compound having the general formula:

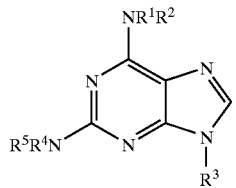

or a pharmaceutically acceptable salt thereof. The prior discussions pertaining to $R^1$, $R^2$, $R^4$, $R^5$ and $R^6$, their definitions and preferred embodiments are fully applicable to the purine analogs used in this method and, thus, will not be repeated.

In accordance with the above method, tumor cells include, but are not limited to, lung, colon, breast, ovarian, prostate and hepatic tumor cells as well as squamous cell carcinomas. In a presently preferred embodiment, the tumor cells are present in a mammalian subject. Mammalian subjects include, but are not limited to, humans, laboratory animals, domestic pets and farm animals. In a further preferred embodiment, the above method further comprises the step of observing for a reduction in the growth of the tumor cells.

In another embodiment, the present invention provides a method of treating cancer, the method comprising administering to a mammalian subject having cancer a therapeutically effective amount of a compound having the general formula:

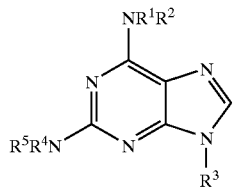

or a pharmaceutically acceptable salt thereof. The prior discussions pertaining to $R^1$, $R^2$ $R^4$, $R^5$ and $R^6$, their definitions and preferred embodiments are fully applicable to the purine analogs used in this method and, thus, will not be repeated.

The compounds of the present invention are useful for treating a wide variety of cancers. Such cancers include, by way of example and not limitation, carcinomas such as pharynx, colon, rectal, pancreatic, stomach, liver, lung, breast, skin, prostate, ovary, cervical, uterine and bladder cancers; leukemias; lymphomas; gliomas; retinoblastomas; and sarcomas. Moreover, in accordance with the above method, mammalian subjects include, but are not limited to, humans, laboratory animals, domestic pets and farm animals.

Purine analogs suitable for use in the methods of the present invention can readily be identified using in vitro and in vivo screening assays. Such assays may screen for the ability of a particular compound to inhibit malignant tumor cell growth or to abolish tumorigenicity of malignant cells in vitro or in vivo. For instance, tumor cell lines can be exposed to varying concentrations of a purine analog of interest, and the viability of the cells can be measured at set time points using the alamar Blue® assay (commercially available from BioSource, International of Camarillo, Calif.). When alamar Blue dye is added to the culture medium, the dye is reduced by cellular mitochondrial enzymes yielding a soluble product with substantially enhanced fluorescence. This fluorescence can be measured with a fluorimeter, whereby the signal is directly proportional to the cell number. Using this information, $IC_{50}$ (concentration of compound lethal to 50% of a cell culture as compared to a control culture) values for the compounds of interest can be readily be calculated.

As will be appreciated by the skilled artisan, many varieties of malignant tumor cell cultures and cell lines can be used to screen for activity, including but not limited to MDA MB 231 (breast), MCF-7 (breast), MDA MB 468 (breast), Siha (squamous cell carcinoma), A549 (non-small cell lung), HL-60 (leukemia) Ovcar-3 (ovarian), etc. In addition, the purine analogs of the present invention can be screened pm the National Cancer Institute panel of 60 human tumor cell lines. Of course, other in vitro and/or in vivo assays to screen for anti-tumor and/or anti-cancer activity known to and used by the skilled artisan can also be employed to identify effective purine analogs useful in the methods of the present invention.

In another preferred embodiment, the purine analogs of the present invention can be used to treat a neurodegenerative disease, the method comprising administering to a mammal having such a disease a therapeutically effective amount of a compound having the general formula:

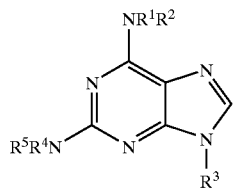

or a pharmaceutically acceptable salt thereof. The prior discussions pertaining to $R^1$, $R^2$, $R^4$, $R^5$ and $R^6$, their definitions and preferred embodiments are fully applicable to the purine analogs used in this method and, thus, will not be repeated.

Neurodegenerative diseases which can be treated using the purine analog compounds of the present invention include, but are not limited to, neurodegenerative pathologies involving multiple neuronal systems and/or brainstem including Alzheimer's disease, AIDS-related dementia, Leigh's disease, diffuse Lewy body disease, epilepsy, Multiple system atrophy, Guillain-Barre syndrome, lysosomal storage disorders such as lipofuscinosis, late-degenerative stages of Down's syndrome, Alper's disease, vertigo as result of CNS degeneration, etc. Other neurodegenerative diseases which can be treated using the purine analogs of the present invention will be readily apparent to those of skill in the art.

In addition, in view of their cell-cycle arresting activities, the purine analogs of the present invention can be used to inhibit undesirable proliferation, including, as described above, cancer, psoriasis, growth of fungi, parasites, viruses, plants, etc. Moreover, the purine analogs of the present invention have apoptosis-inducing effects in actively dividing cells and, thus, this property can be advantageously used to treat various disease states associated with undesirable proliferation. Such uses are described, for example, in Meijer, L., *Trends in Cell Biology* (1986), 6:393–397, the teachings of which are incorporated herein by reference for all purposes.

In addition to the foregoing, the purine analogs of the present invention can be used in vitro as molecular tools and probes. For instance, since CDK inhibitors arrest cells both in G1 and late G2/early prophase, they can be used to synchronize cells when used preferably in combination with another synchronizing agent/method (e.g., when used in combination with aphidicolin). In addition, immobilized CDK inhibitors can be used for affinity purification/depletion of CDKs from cellular extracts. Such purine analogs will be particularly useful for massive purification of expressed CDKs (for crystallography or screening purposes). In addition, such purine analogs are useful for comparative analysis of CDKs extracted from cells at difference developmental or cell-cycle stages (variation of concentration, kinase activity, post-translational modifications, etc.).

D. Pharmaceutical Formulations/Routes of Administration

The compounds, i.e., purine analogs, of the present invention can be administered to a mammal, e.g., a human patient, alone, in the form of a pharmaceutically acceptable salt, or in the form of a pharmaceutical composition where the compound is mixed with suitable carriers or excipient(s) in a therapeutically effective amount, e.g., at doses effective to inhibit a protein kinase or a cellular process or achieve amelioration of symptoms of a disease associated with a protein kinase.

The compounds of this invention can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the compounds can be achieved in various ways, including oral, buccal, rectal, parenteral, intraperitoneal, intradermal, transdermal, intracheal, etc., administration. Moreover, the compound can be administered in a local rather than systemic manner, for example via injection of the compound directly into a solid tumor, often in a depot or sustained release formulation. In addition, the compounds can be administered in a targeted drug delivery system, for example, in a liposome coated with tumor-specific antibody. Such liposomes will be targeted to and taken up selectively by the tumor.

The purine analogs of the present invention can be administered alone, in combination with each other, or they can be used in combination with other known compounds (e.g., other drugs, such as anti-cancer drugs (e.g., AZT), anti-mitotics, anti-inflammatories, antibiotics, corticosteroids, vitamins, etc.). More particularly, the compound of the present invention can be used in conjunctive therapy with other known chemotherapeutic or antineoplastic agents (e.g., vinca alkaloids, antibiotics, antimetabolites, platinum coordination complexes, etc.). For instance, the compounds of the present invention can be used in conjunctive therapy with a vinca alkaloid compound, such as vinblastine, vincristine, taxol, etc.; an antibiotic, such as adriamycin (doxorubicin), dactinomycin (actinomycin D), daunorubicin (daunomycin, rubidomycin), bleomycin, plicamycin (mithramycin) and mitomycin (mitomycin C), etc.; an antimetabolite, such as methotrexate, cytarabine (AraC), azauridine, azaribine, fluorodeoxyuridine, deoxycoformycin, mercaptopurine, etc.; or a platinum coordination complex, such as cisplatin (cis-DDP), carboplatin, etc. In addition, those of skill in the art will appreciate that the compounds of the present invention can be used in conjunctive therapy with other known chemotherapeutic or antineoplastic compounds. In pharmaceutical dosage forms, the compounds may be administered in the form of their pharmaceutically acceptable salts, or they may also be used alone or in appropriate association, as well as in combination with other pharmaceutically active compounds.

Suitable formulations for use in the present invention are found in *Remington's Pharmaceutical Sciences* (Mack Publishing Company, Philadelphia, Pa., 17th ed. (1985)), which is incorporated herein by reference. Moreover, for a brief review of methods for drug delivery, see, Langer, *Science* 249:1527–1533 (1990), which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the compounds of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

For any compound used in the method of the invention, a therapeutically effective dose can be estimated initially from cell culture assays. For example, a dose can be formulated in animal models to achieve a circulating concentration range that includes the $IC_{50}$ as determined in cell culture (i.e., the concentration of test compound that is lethal to 50% of a cell culture), or the $IC_{100}$ as determined in cell culture (i.e., the concentration of compound that is lethal to 100% of a cell culture). Such information can be used to more accurately determine useful doses in humans. Initial dosages can also be estimated from in vitro or in vivo data.

Initial dosages can also be formulated by comparing the effectiveness of the compounds described herein in cell culture assays with the effectiveness of known drugs. For instance, when use as anticancer agents, initial dosages can be formulated by comparing the effectiveness of the compounds described herein in cell culture assays with the effectiveness of known anticancer drugs such as vincristine. In this method, an initial dosage can be obtained by multiplying the ratio of effective concentrations obtained in cell culture assay for the a compound of the present invention and a known anti-cancer drug by the effective dosage of the known anti-cancer drug. For example, if a compound of the present invention is twice as effective in cell culture assay than vincristine (i.e., the $IC_{50}$ of that compound is equal to one-half the $IC_{50}$ of vincristine in the same assay), an initial effective dosage of the compound of the present invention would be one-half the known dosage for vincristine. Using these initial guidelines one having ordinary skill in the art could determine an effective dosage in humans.

Moreover, toxicity and therapeutic efficacy of the compounds described herein can be determined by standard pharmaceutical procedures in cell cultures or experimental animals, e.g., by determining the $LD_{50}$, (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. Compounds which exhibit high therapeutic indices are preferred. The data obtained from these cell culture assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics*, Ch. 1, p. 1).

Dosage amount and interval may be adjusted individually to provide plasma levels of the active compound which are sufficient to maintain therapeutic effect. Usual patient dosages for oral administration range from about 50–2000 mg/kg/day, commonly from about 100–1000 mg/kg/day, preferably from about 150–700 mg/kg/day and most preferably from about 250–500 mg/kg/day. Preferably, therapeutically effective serum levels will be achieved by administering multiple doses each day. In cases of local administration or selective uptake, the effective local concentration of the drug may not be related to plasma concentration. One having skill in the art will be able to optimize therapeutically effective local dosages without undue experimentation.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1 illustrates a general synthetic scheme for producing the purine derivatives of the invention on a solid support. The solid-phase synthesis strategy exemplified by Scheme 2 involves attaching the growing compound to the solid-support via the side-chain at position 2 of the purine ring structure.

Library #1:

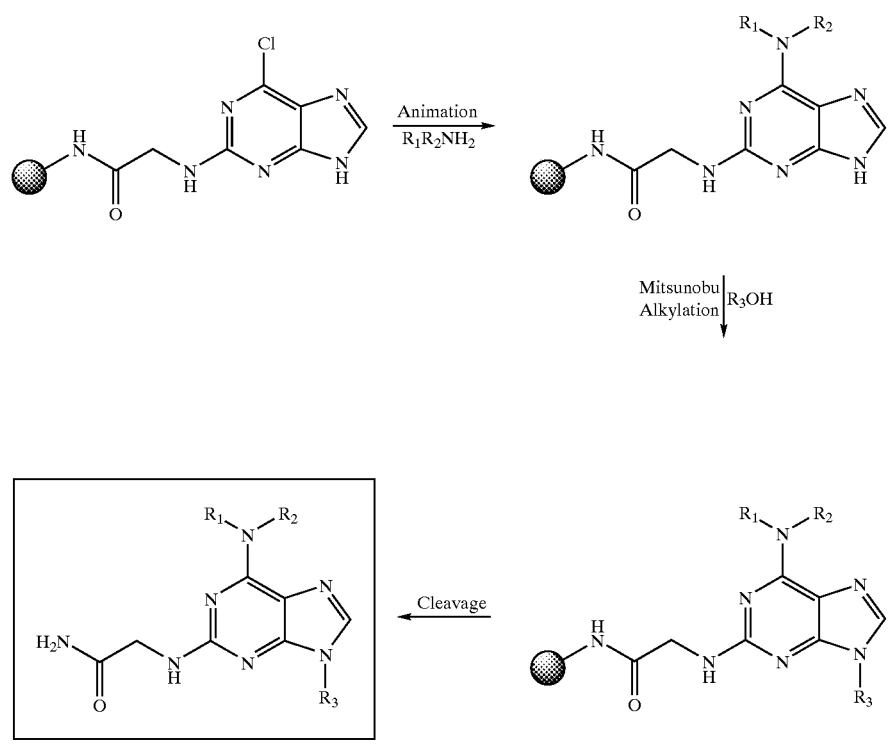

Scheme 1

Example 2

Example 2 illustrates a generalized synthetic route to purine derivatives on a solid support. The solid-phase synthesis strategy exemplified by Scheme 2 involves attaching the growing compound to the solid-support via the side-chain at position 9 of the purine ring structure.

Library #2:
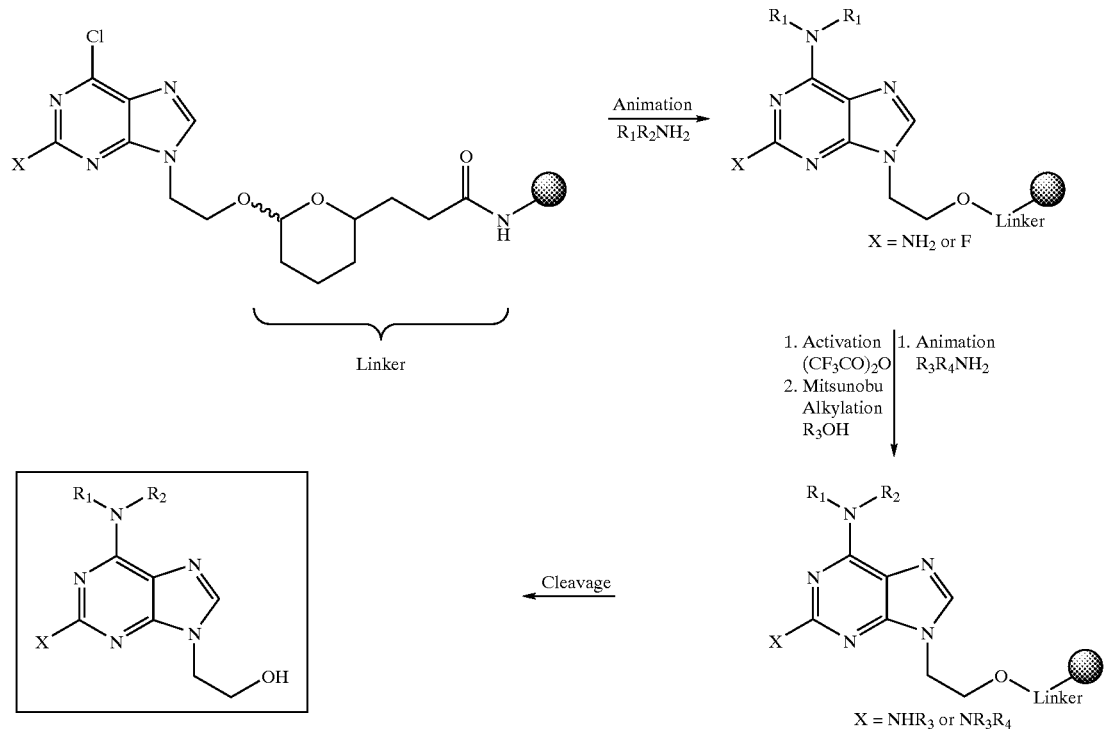
Example 3
Example 3 illustrates a general route to purine derivatives synthesized on a solid support. The route exemplified by Scheme 3 involves attaching the growing compound to the solid-support via the substituent at the 6-position of the purine ring.
Library #3:
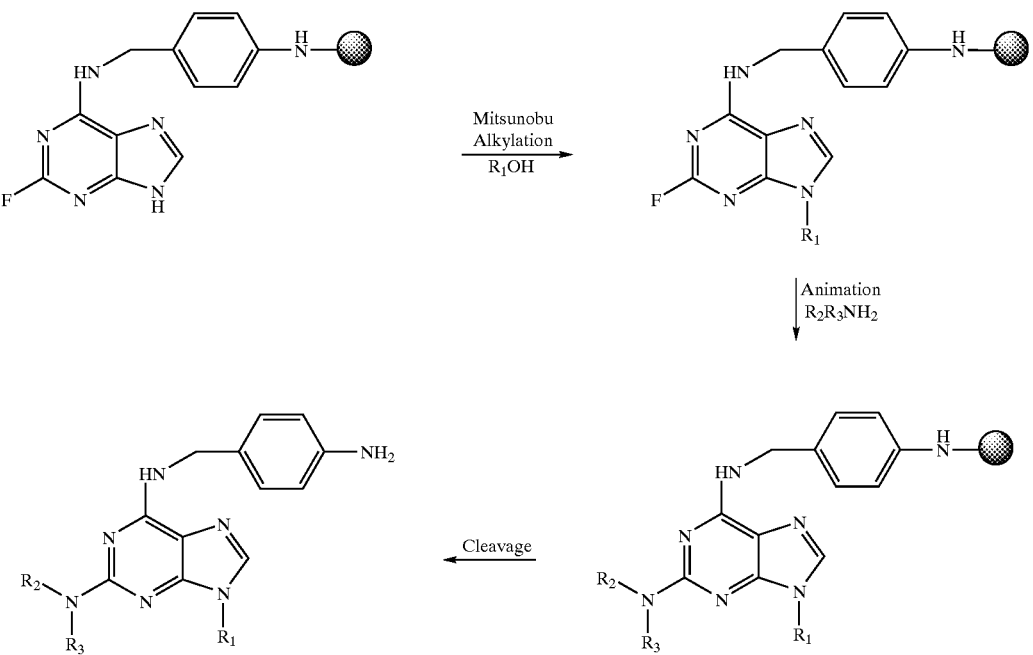

Example 4

Example 4 details the alkylation of position 9 of a purine nucleus. The synthetic route is summarized in Scheme 4.

Scheme 4

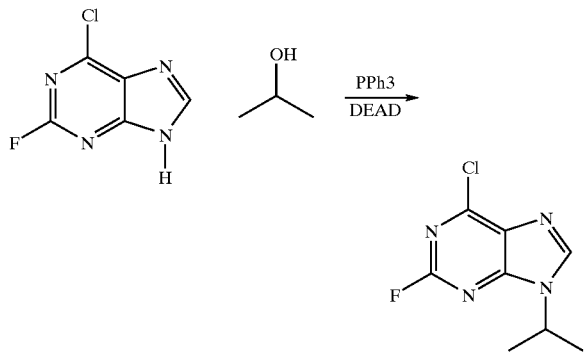

2-Fluoro-6-chloropurine (900 mg 5.20 mmol) and PPh$_3$ (3.0 g, 10.4 mmol) were combined in a flame-dried flask under N$_2$. Freshly distilled THF (60 mL) was added followed by 2-propanol (800 µL, 10.4 mmol). The mixture was cooled to −10° C. in an ethylene glycol/dry ice bath. DEAD (850 µL, 10.4 mmol) was added over 10 min. The mixture was stirred at −10° C. and gradually returned to room temperature over 3 hours.

The reaction was quenched by adding water (500 µL) to the reaction mixture. The solvent was removed in vacuo to viscous yellow oil. The oil was azeotroped with CH$_2$Cl$_2$ (2×10 mL) to remove trace THF. Purification was effected by column chromatography on silica gel eluted with CH$_2$Cl$_2$. The CH$_2$Cl$_2$ was removed from the desired fraction. The desired product was isolated in 57% yield as a white powder.

Example 5

Example 5 illustrates the synthetic route to animation of the

Scheme 5

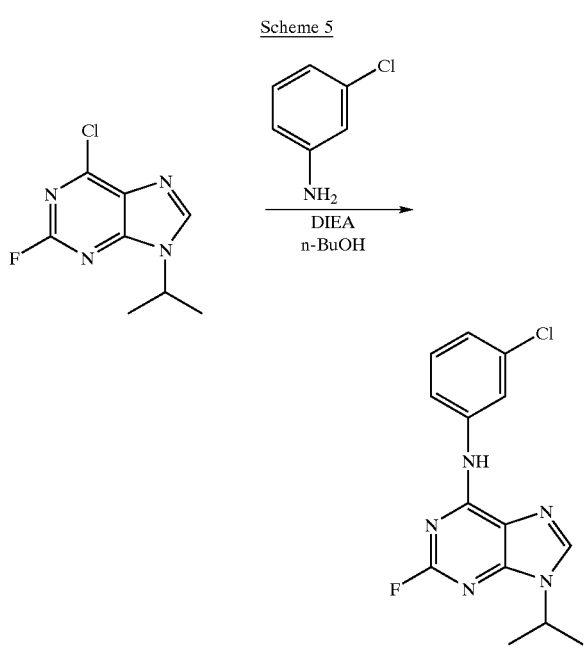

The compound from Example 4 (3.75 g, 17.47 mmol) was combined with 3-chloroaniline (1.85 mL, 17.47 mmol) and diisopropylethylamine (3.05 mL, 17.47 mmol) in n-BuOH. The reaction mixture was heated to 70° C.–80° C. for 11 hours. The n-BuOH was removed under vacuum and the resulting residue was suspended in H$_2$O to produce a slurry. The product was isolated by filtration, washed with small portions of CH$_2$Cl$_2$ and Et$_2$O. The product was dried first under a stream of air and then under vacuum. The desired product was isolated in 58% yield.

Example 6

Example 6 details the amination of the 2-position of the purine ring system. The synthetic route is illustrated in Scheme 6.

Scheme 6

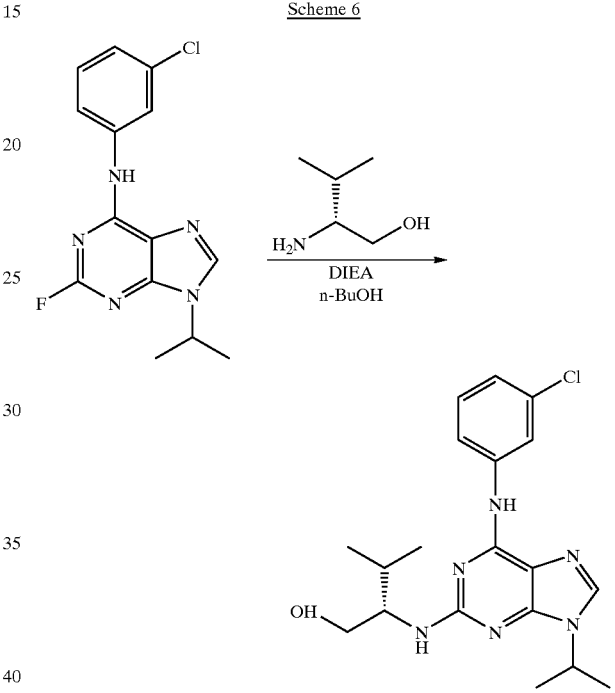

The compound from Example 5 (1.55 g, 5.10 mmol), 2-amino-3-methyl-1-butanol (559 µL, 5.10 mmol) and diisopropylethylamine (892 µL, 5.10 mmol) were combined in n-BuOH. The mixture was heated to approximately 100° C. The solvent was removed under reduced pressure and the residue purified by silica gel chromatography using 99:1 CH$_2$Cl$_2$:MeOH. The desired product was isolated in 71% yield.

The above examples illustrate both general and specific methods for synthesizing a wide array of the purine derivatives of the present invention.

Example 7

This example illustrates a CDK2/CYCLIN A Microtiter Protein Kinase Assay which can be used to screen the purine analogs of the present invention for inhibitory activity.

1. Required Buffers and Solutions
   a. Buffer A: 80 mM Tris (pH=7.2) mM MgCl$_2$ Recipe: 4.84 g Tris (F.W.=121.1 g/mol) 4.07 g MgCl$_2$ (F.W.= 203.31 g/mol) dissolved in 500 mL of ddH$_2$O. pH adjusted to 7.2 with HCl.
   b. Histone H1 solution: 0.45 mg/ml Histone H1 in 20 mM HEPES pH=72. Recipe: 5 mg of Histone H1 in 11.111 mL of 20 mM HEPES pH=7.2. 477 mg of HEPES provided in 1 mL aliquots. Store at −80° C.

c. ATP solution: 90 μM ATP, 300 μg/mL BSA, 3 mM DTT. Recipe: 9.25 mg DTT, 1.01 mg ATP (F.W.=560 g/mol), 6 mg BSA dissolved in 20 mL ddH₂O. Provided in 1 mL aliquots. Store at −80° C.

d. CDK2 solution: 10 mM HEPES pH=7.2, 25 mM NaCl, 0.5 mM DTT, 10% glycerol. Provided in 192 μL aliquots. Store at −80° C.

2. Stepwise Description of Assay.

a. Prepare solutions of inhibitors at three times the desired final assay concentration in ddH₂O 15% DMSO by volume.

b. Dispense 20 μL of inhibitors to the well of a microtiter-formatted assay tray.

c. Thaw Histone H1 solution (1 mL aliquot), ATP solution (1 mL aliquot) and CDK2 solution (192 μL aliquot).

d. Dilute 192 μL of CDK2 solution into 2.1 mL of buffer A. Swirl to mix. Dispense 20 μL of this solution to each well using a multichannel pipetman. (Note it is important to have a fairly pointed trough for loading the multichannel to avoid running out of solution.)

e. Mix 1 mL of Histone H1 solution with 1 mL of the ATP solution in a 10 mL screw cap tube. Swirl to mix. Add 2–3 μL (Depending on how fresh you hot ATP is) of γ-³²P-ATP (10 μCi/mL). Mix thoroughly to get even distribution of hot ATP but watch out for BSA frothing! Dispense to wells with multichannel pipetman; mix the solution in the wells half a dozen times with the multichannel pipetman.

f. Let reactions proceed for 30 minutes. While reactions are running you can i) Presoak a 9×12 cm piece of nitrocellulose (0.22 Micron) in water for 10 minutes.

ii) Load the nitrocellulose paper onto the dot blot. Screw the four clamps down (do this in a diagonal fashion) till they are finger tight. Then apply a vacuum and continue to tighten the screws until they are tight. Turn off the vacuum and load 100 μL of water into each well of the dot blot to rehydrate the membrane. Apply a weak vacuum to remove the excess water, but be careful not to dry out the membrane.

iii) Just before the 30 minutes is up add 35 μL of 10% TCA to each well of the dot blot.

g. Using the multichannel pipetman transfer 35 μL of the reaction mixtures to each well of the dot blot in the same fashion as the ATP was dispensed (to insure equal reaction times).

h. Add an additional 35 μL of 10% TCA and apply a weak vacuum until the wells are free of liquid. Repeat the process of adding 35 μL of 10% TCA and draining with the vacuum two more times. Remember to turn off vacuum when the wells are free of liquid or when you are refilling.

i. Add 35 μL of water to each well of the dot blot and apply a weak vacuum until the wells are free of liquid. Carry out this process a total of four times.

j. Transfer the nitrocellulose membrane from the dot blot apparatus into a small tray containing enough water to cover the membrane. Let the membrane sit in the water for ten minutes then decant. Wash the membrane in this fashion with three batches of water.

k. Let the membrane dry completely before analysis with the phosphoimager.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purpose.

What is claimed is:

1. A compound having a formula which is a member selected from the group consisting of:

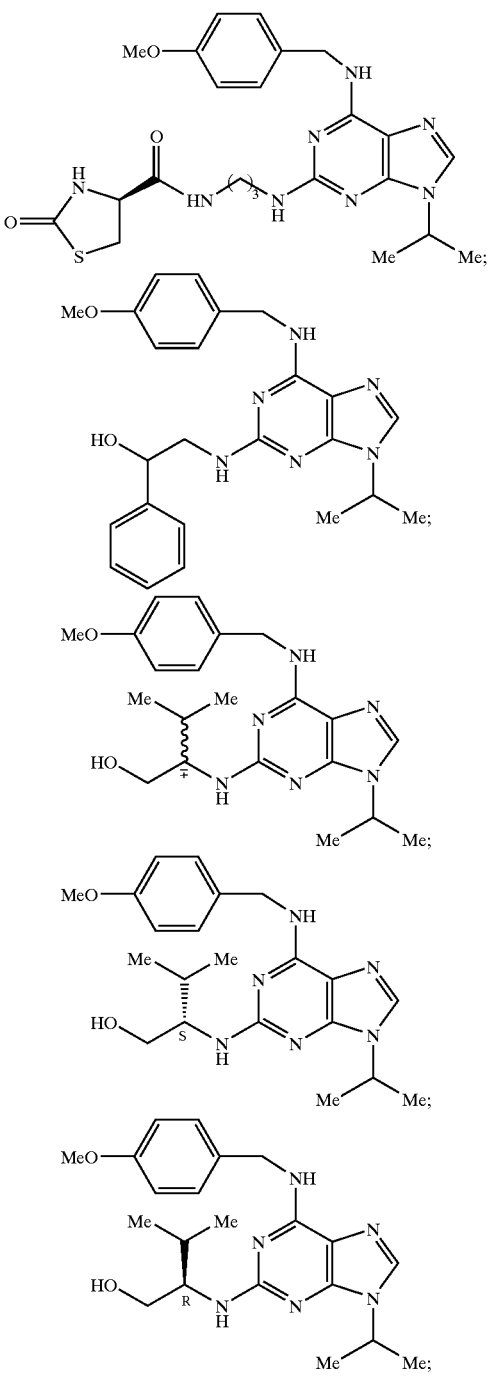

-continued

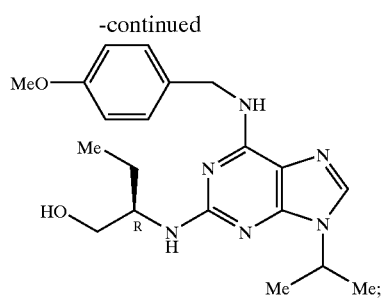

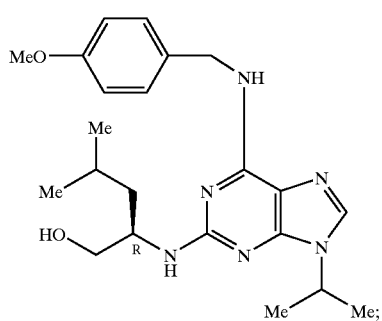

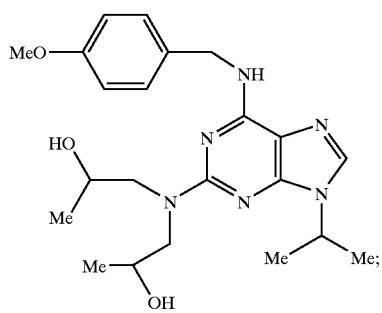

-continued

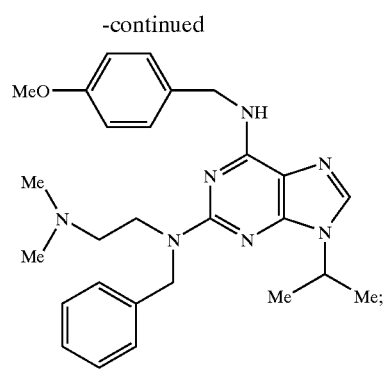

and

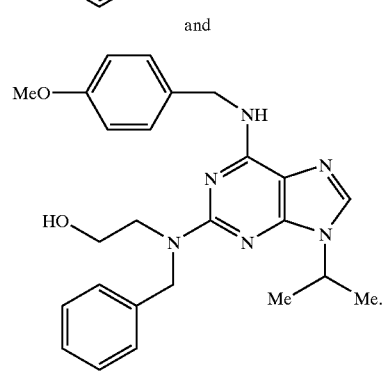

2. A pharmaceutical composition comprising a compound according to claim 1 and a pharmaceutically acceptable excipient.

3. A method of inhibiting growth of a tumor cell which is a member selected from the group consisting of lung, colon, breast, ovary, prostate and liver, said method comprising contacting said tumor cell with an amount of a compound according to claim 1 effective to inhibit said growth of said tumor cell.

4. The method according to claim 3, wherein said tumor cell is in a mammalian subject.

\* \* \* \* \*